(12) United States Patent
Hazlebeck et al.

(10) Patent No.: US 7,687,261 B2
(45) Date of Patent: Mar. 30, 2010

(54) PHOTOSYNTHETIC OIL PRODUCTION IN A TWO-STAGE REACTOR

(75) Inventors: David A. Hazlebeck, El Cajon, CA (US); Eric H. Dunlop, Paradise (AU)

(73) Assignee: General Atomics, San Diego, CA (US)

( * ) Notice: Subject to any disclaimer, the term of this patent is extended or adjusted under 35 U.S.C. 154(b) by 518 days.

(21) Appl. No.: 11/549,532

(22) Filed: Oct. 13, 2006

(65) Prior Publication Data

US 2008/0086937 A1    Apr. 17, 2008

(51) Int. Cl.
C12M 1/00    (2006.01)
(52) U.S. Cl. .............. 435/289.1; 435/293.1; 435/257.1; 435/294.1; 47/1.4
(58) Field of Classification Search .............. 435/292.1, 435/293.1, 294.1; 47/1.4; 210/606, 602, 210/629, 926; 366/176.1, 181.5
See application file for complete search history.

(56) References Cited

U.S. PATENT DOCUMENTS

| | | | |
|---|---|---|---|
| 2,658,310 A | 11/1953 | Cook | |
| 2,732,661 A | 1/1956 | Spoehr et al. | |
| 2,732,663 A * | 1/1956 | Dewey, III | .................... 47/1.4 |
| 2,854,792 A | 10/1958 | Juda | |
| 2,949,700 A | 8/1960 | Kathrein | |
| 3,108,402 A | 10/1963 | Kathrein | |
| 3,195,271 A | 7/1965 | Golueke et al. | |
| 3,218,758 A | 11/1965 | Konikoff | |
| 3,446,488 A | 5/1969 | Mail et al. | |
| 3,468,057 A | 9/1969 | Buisson et al. | |
| 3,521,400 A | 7/1970 | Ort | |
| 3,839,198 A * | 10/1974 | Shelef | .................... 210/602 |
| 3,955,318 A | 5/1976 | Hulls | |
| 3,958,364 A | 5/1976 | Schenck et al. | |
| 4,087,936 A | 5/1978 | Savins et al. | |
| 4,236,349 A | 12/1980 | Ramus | |
| 4,253,271 A | 3/1981 | Raymond | |
| 4,417,415 A | 11/1983 | Cysewski et al. | |
| 4,958,460 A | 9/1990 | Nielson et al. | |
| 5,330,913 A | 7/1994 | Nakayama | |
| 5,951,875 A | 9/1999 | Kanel et al. | |
| 6,000,551 A | 12/1999 | Kanel et al. | |
| 6,524,486 B2 | 2/2003 | Borodyanski et al. | |
| 6,667,171 B2 | 12/2003 | Bayless et al. | |

OTHER PUBLICATIONS

NREL/TP-580-24190, A Look Back at the U.S. Department of Energy's Aquatic Species Program; Biodiesel from Algae, Jul. 1998.

* cited by examiner

*Primary Examiner*—William H Beisner
*Assistant Examiner*—Michael Hobbs
(74) *Attorney, Agent, or Firm*—Nydegger & Associates

(57) ABSTRACT

A system and method are provided for producing algae with high oil content. The system includes a chemostat formed with a conduit for growing algae, an input port for feeding a medium into the conduit, and an output port for passing an effluence from the conduit. Further, the chemostat includes a paddlewheel or other device that moves the medium around the conduit. Also, the system includes a plug flow reactor for receiving the effluence from the chemostat. In order to trigger high oil production in the algae, a modified nutrient mix is added to the effluence in the plug flow reactor. Specifically, the modified nutrient mix comprises a limited amount of a selected constituent to trigger oil production in the algae. Further, the system includes an algae separator for removing high oil content algae from the plug flow reactor.

14 Claims, 1 Drawing Sheet

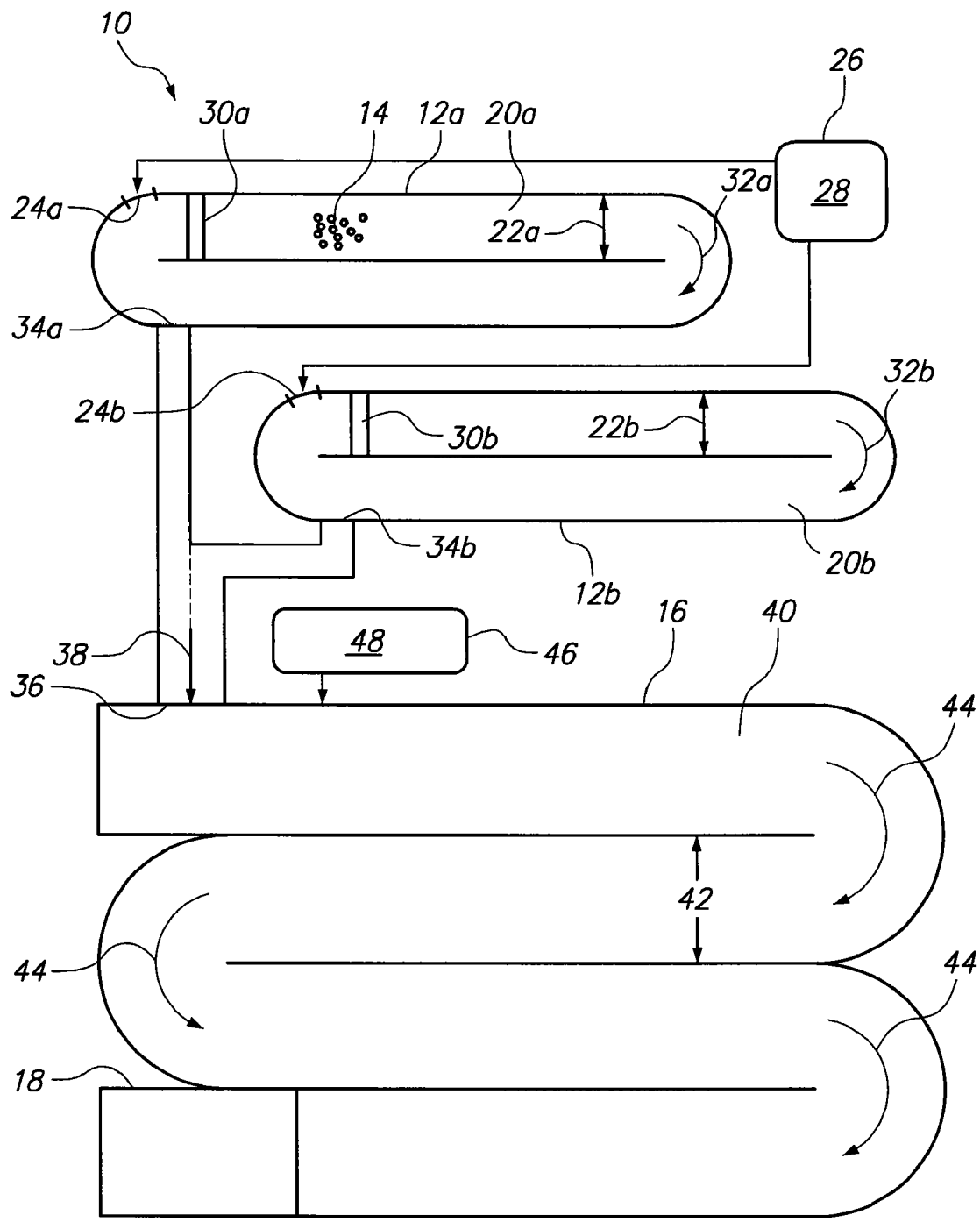
FIGURE

PHOTOSYNTHETIC OIL PRODUCTION IN A TWO-STAGE REACTOR

FIELD OF THE INVENTION

The present invention pertains generally to photosynthetic oil production in algae. More particularly, the present invention pertains to the treatment of algae to maximize algae cell growth as well as the production of oil within the algae cells. The present invention is particularly, but not exclusively, useful as a system and method for producing high oil content algae cells in a two-stage reactor.

BACKGROUND OF THE INVENTION

As worldwide petroleum deposits decrease, there is rising concern over shortages and the costs that are associated with the production of hydrocarbon products. As a result, alternatives to products that are currently processed from petroleum are being investigated. In this effort, biofuel such as biodiesel has been identified as a possible alternative to petroleum-based transportation fuels. In general, a biodiesel is a fuel comprised of mono-alkyl esters of long chain fatty acids derived from plant oils or animal fats. In industrial practice, biodiesel is created when plant oils or animal fats are reacted with an alcohol, such as methanol.

For plant-derived biofuel, solar energy is first transformed into chemical energy through photosynthesis. The chemical energy is then refined into a usable fuel. Currently, the process involved in creating biofuel from plant oils is expensive relative to the process of extracting and refining petroleum. It is possible, however, that the cost of processing a plant-derived biofuel could be reduced by maximizing the rate of growth of the plant source. Because algae is known to be one of the most efficient plants for converting solar energy into cell growth, it is of particular interest as a biofuel source. Importantly, the use of algae as a biofuel source presents no exceptional problems, i.e., biofuel can be processed from oil in algae as easily as from oils in land-based plants.

While algae efficiently transforms solar energy into chemical energy via a high rate of cell growth, a high rate of cell growth alone is not sufficient to make algae-based biofuel cost efficient. Rather, the efficient production of biofuel further requires a maximization of the rate of oil production within the algae cells. Currently, the production of biofuel from algae is limited by a failure to maximize both algae cell growth and the production of oil within the algae cells. Specifically, the conditions necessary to facilitate a fast growth rate for algae cells have been found to hinder the production of oil within those algae cells. Likewise, the conditions necessary to facilitate a fast rate of oil production within algae cells have been found to hinder the growth of the algae cells.

In greater detail, the biochemical process of photosynthesis provides algae with the ability to convert solar energy into chemical energy. During cell growth, this chemical energy is used to drive synthetic reactions, such as the formation of sugars or the fixation of nitrogen into amino acids for protein synthesis. Excess chemical energy is stored in the form of fats and oils as triglycerides. Therefore, it can be seen that cell growth and triglyceride production compete for the same chemical energy. As a result, the simultaneous rates of growth and oil production are inversely related. In the past, emphasis has been on algae cell growth and the resulting low oil production has been accepted as a necessary condition.

In light of the above, it is an object of the present invention to provide a system and method for maximizing both the cell growth of algae and the production of oil within the algae cells. For this purpose, a number of systems have been developed, such as those disclosed in co-pending U.S. patent application Ser. No. 11/549,541 for an invention entitled "Photosynthetic Carbon Dioxide Sequestration and Pollution Abatement," co-pending U.S. patent application Ser. No. 11/549,552 for an invention entitled "High Photoefficiency Microalgae Bioreactors" and co-pending U.S. patent application Ser. No. 11/549,561 for an invention entitled "Photosynthetic Oil Production with High Carbon Dioxide Utilization," which are filed concurrently herewith and assigned to the same assignee as the present invention, and are hereby incorporated by reference. Another object of the present invention is to provide a two stage system with a first stage for maximizing algae cell growth and a second stage for maximizing oil production within the algae cells. Still another object of the present invention is to provide a system for growing algae cells in which oil production in the cells is selectively triggered. Another object of the present invention is to provide a two stage reactor system for growing algae with a high oil content that defines a flow path for continuous movement of the algae during cell growth and oil production. Yet another object of the present invention is to provide a system and method for producing algae with high oil content that is simple to implement, easy to use, and comparatively cost effective.

SUMMARY OF THE INVENTION

In accordance with the present invention, a system is provided for producing algae with high oil content, i.e., an oil content greater than at least 30%, and preferably greater than 60%, of the dry weight of the algae. Structurally, the system includes a first stage reactor for growing algae cells and a second stage reactor for treating the algae cells to foster oil production. For purposes of the present invention, the first stage reactor is a continuously-stirred flow reactor that has an input port, a conduit, and an output port. Preferably, the conduit is formed by an endless, open raceway that receives and holds a medium. A paddlewheel spanning the conduit is provided to circulate the medium through the conduit.

For the present invention, the second stage reactor is positioned relative to the first stage reactor to receive an effluent containing algae cells from the first stage reactor. Specifically, the second stage reactor includes an input port that receives the effluent from the output port of the first stage reactor. Further, the second stage reactor includes a conduit for continuously moving the effluent downstream under the influence of gravity. For purposes of the present invention, the second stage reactor is a plug flow reactor in the form of an open raceway. In addition to the first and second stage reactors, the system includes an algae separator for removing the algae cells from the conduit of the second stage reactor.

In operation, a medium with a nutrient mix is fed into the conduit of the first stage reactor. The medium is moved around the first stage reactor at a preferred fluid flow velocity of approximately 50 centimeters per second by the paddlewheel. During the circulation of the medium, algae cells grow using solar energy and nutrients provided in the medium. It is preferred that the first stage reactor be designed to grow algae cells indefinitely. Specifically, after a steady state is reached by filling the first stage reactor with the circulating medium, both the conditions and the number of the algae cells within the first stage reactor are held substantially constant. This is accomplished by adding a constant flow of medium to the first stage reactor through the input port while removing algae-laden medium from the output port as an effluent.

After the effluence is removed from the first stage reactor, it is received in the second stage reactor and is treated in order to trigger the production of oil in the form of triglycerides in the algae cells. For instance, a modified nutrient mix may be fed into the conduit of the second stage reactor to induce oil production. For this purpose, the modified nutrient mix will include only a limited amount of a selected constituent, such as nitrogen or phosphorous, which is necessary for cell growth. When faced with the shortage of the selected constituent, the algae cells respond by using the available nutrients and energy to create triglycerides. In this manner, oil production by the algae is triggered. In another embodiment, the algae cells may be allowed to completely utilize certain nutrients remaining in the effluence as the effluence passes through the conduit of the second stage reactor. Specifically, the algae cells may convert, for example, all of the nitrogen in the effluence into cell matter during cell growth. After no nitrogen remains in the effluence, the algae cells cease cell growth, and instead begin the production of triglycerides. In this case, the modified nutrient mix may include only water to compensate for evaporation, or it may include other nutrients such as glycerin to aid in triglyceride production.

After passing along the conduit of the second stage reactor, the algae is removed from the second stage reactor by an algae separator. To facilitate this removal, the algae separator may be dimensioned to slow the fluid flow velocity of the effluence to promote segregation and flocculation of the algae growth. Further, the modified nutrient mix may include a limited amount of a predetermined constituent to further trigger flocculation of the algae cells. Depending on the oil content of the algae cells, the algae may settle at the bottom or rise to the top of the effluence in the conduit.

BRIEF DESCRIPTION OF THE DRAWINGS

The novel features of this invention, as well as the invention itself, both as to its structure and its operation, will be best understood from the accompanying drawing, taken in conjunction with the accompanying description, in which the FIGURE is an overhead view of the system for producing algae with high oil content in accordance with the present invention.

DESCRIPTION OF THE PREFERRED EMBODIMENTS

Referring to the FIGURE, a system for producing algae with high oil content in accordance with the present invention is shown and generally designated 10. As shown, the system 10 includes a plurality of first stage reactors 12 for growing algae cells (exemplary cells depicted at 14). In the FIGURE, suffixes "a" and "b" are applied to reference numerals to denote the similar elements for each illustrated first stage reactor 12. Further, the system 10 includes a second stage reactor 16 for treating the algae cells 14 to trigger cell production of triglycerides. Preferably, and as shown, both the first stage reactors 12 and the second stage reactor 16 are open raceways, though closed systems are also contemplated. Open raceway systems 10 are often preferred because such open systems 10 can cover several acres of land to optimize economies of scale. For purposes of the present invention, the system 10 includes an algae separator 18 for removing the algae cells 14 from the second stage reactor 16.

As shown in the FIGURE, each first stage reactor 12 includes a conduit 20. Preferably, each conduit 20 has a width 22 within the range of about five to fifty meters, and preferably about ten meters, and a depth of about five to one hundred centimeters. As further shown, each conduit 20 is provided with an input port 24. For purposes of the present invention, each input port 24 is in communication with a reservoir 26 holding a medium 28 including a nutrient mix. Preferably, the nutrient mix includes phosphorous, nitrogen, sulfur, carbonates, dissolved carbon dioxide and the numerous trace elements necessary to support algae growth. Further, the first stage reactor 12 is provided with a paddlewheel 30 for causing the medium 28 to continuously move through the conduit 20 in the direction of arrow 32 at a predetermined fluid flow velocity. Also, each conduit 20 is provided with an output port 34 in communication with the second stage reactor 16.

As shown, the second stage reactor 16 includes an input port 36 for receiving an effluence (indicated by arrow 38) laden with algae cells 14 from the output port 34 of each first stage reactor 12. As further shown; the second stage reactor 16 includes a conduit 40 for passing the effluence 38 with algae cells 14 downstream in the direction of arrows 44. The flow of the effluence 38 is due solely to gravity and the force of the incoming effluence 38 from the first stage reactors 12. Preferably, the second stage reactor 16 is a plug flow reactor with a substantially fixed residence time of about one to four days. In the illustration, the conduit 40 has a width 42 of about twenty meters and a depth of about five to one hundred centimeters, similar to the depths of the conduits 20 of the first stage reactors 12. While the width 42 of the conduit 40 is illustrated to be equal to the sum of the widths 22 of the conduits 20 of the first stage reactors 12, this relationship is not required. Specifically, the depths and flow rates of the conduits 20 of the first stage reactors 12 and the conduit 40 of the second stage reactor 16 may be varied such that no set relationship exists between the widths 22 of the conduits 20 and the width 42 of the conduit 40. Nevertheless, it is noted that the flow rates of the conduits 20, 40 may be controlled through design of the conduit depths and widths as well as through the rate of addition of medium. It is further noted that the depth of the conduit 40 may be gradually decreased in the direction of arrows 44 to account for evaporation without requiring the addition of water.

For purposes of the present invention, the system 10 is provided with a reservoir 46 that holds a modified nutrient mix 48. As shown, the reservoir 46 is positioned to deliver the modified nutrient mix 48 to the conduit 40 of the second stage reactor 16. In order to manipulate the cellular behavior of algae cells 14 within the second stage reactor 16, the modified nutrient mix 48 may contain a limited amount of a selected constituent, such as nitrogen or phosphorous. For instance, the nutrient mix 48 may contain no nitrogen.

In the FIGURE, the algae separator 18 is shown in fluid communication with the conduit 40 of the second stage reactor 16. For purposes of the present invention, the algae separator 18 separates the algae cells 14 from the effluence 38 and any remaining nutrients therein through flocculation and/or filtration. To facilitate settling of the algae cells 14, the algae separator 18 may include an increased flow volume by having an increased depth relative to the second stage reactor 16. Also, the separator 18 may include a belt press or some other device for removing water from the mass of algae cells 14.

In operation, the medium 28 with the nutrient mix is initially fed to the conduit 20 of each first stage reactor 12 until each conduit 20 is full. Thereafter, the medium 28 with the nutrient mix is continuously fed to each first stage reactor 12 at a selected rate, thereby causing effluence 38 to be selectively released through each first stage reactor's output port 34. For purposes of the present invention, each first stage reactor 12 may be considered to be a chemostat that is designed to grow algae cells 14 indefinitely. Further, the conditions in each first stage reactor 12 are maintained for maximum algal growth. To maintain the desired conditions, the medium 28 and algae cells 14 are moved around each conduit 20 by the respective paddlewheel 30 at a preferred fluid flow velocity of approximately 50 centimeters per second. Further, the amount of algae cells 14 within each first stage reactor 12 are kept substantially constant by continuously feeding the medium 28 with nutrient mix and continuously removing algae cells 14 from the conduit 20 in the effluence 38. Under preferred conditions, approximately ten to fifty grams of algae per liter of fluid circulate in the conduit 20 of each first stage reactor 12. Preferably, the residence time for algae cells 14 in each first stage reactor 12 is about one to ten days.

After the effluence 38 is received in the conduit 40 of the second stage reactor 16, it moves downstream in the direction of arrows 44 in a plug flow regime. Preferably, the effluence 38 moves through the conduit 40 of the second stage reactor 16 at a rate of between ten and one hundred centimeters per second. Further, as the effluence 38 moves downstream, the modified nutrient mix 48 is added to the conduit 40 of the second stage reactor 16. As stated above, the modified nutrient mix 48 contains a limited amount of a selected constituent, such as nitrogen or phosphorous. The absence or small amount of the selected constituent causes the algae cells 14 to focus on energy storage rather than growth. As a result, the algae cells 14 form triglycerides. Upon reaching the algae separator 18, the algae cells 14 have typically produced sufficient oil to be at least 30%, and preferably greater than 60% oil by dry weight.

At the algae separator 18, the depth of the conduit 40 is increased. The corresponding increase in fluid flow area allows the algae cells 14 to settle or rise, depending on the oil content of the cells 14. Alternatively, dissolved air flotation can be used to segregate the algae cells 14 from the effluence 38. Thereafter, the algae separator 18 removes the algae cells 14 from the second stage reactor 16 for processing. In certain embodiments, the modified nutrient mix 48 may include a limited amount of a predetermined constituent to trigger flocculation of the algae cells 14 in the second stage reactor 16. The predetermined constituent may be the same as the selected constituent such that a shortage of nitrogen, for example, causes both the production of triglycerides and the flocculation of the algae cells 14.

While the particular Photosynthetic Oil Production in a Two-Stage Reactor as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A system for producing algae with high oil content which comprises:
    at least one chemostat formed with an open raceway conduit for growing algae therein, the chemostat having an input port for feeding a medium with a nutrient mix into the conduit for maximum algae growth, and having an output port for passing an effluence with algae growth from the conduit of the chemostat;
    a paddlewheel means for continuously moving the medium through the conduit of the chemostat at a predetermined fluid flow velocity;
    a plug flow reactor formed with an open raceway conduit having an input port for receiving the effluence with algae growth from the chemostat for a gravity flow of the effluence through the plug flow reactor;
    a means for adding a modified nutrient mix to the effluence with algae growth in the plug flow reactor, wherein the modified nutrient mix comprises a limited amount of a selected constituent to trigger high oil production in the algae growth; and
    an algae separator in fluid communication with the conduit of the plug flow reactor for removing algae growth with high oil content directly therefrom.

2. A system as recited in claim 1 wherein the selected constituent is selected from a group consisting of nitrogen and phosphorous.

3. A system as recited in claim 1 wherein the algae separator is dimensioned to slow the fluid flow velocity of the effluence received therein from the conduit of the plug flow reactor to promote settling and flocculation of the algae growth.

4. A system as recited in claim 1 wherein the means for moving the medium is a paddlewheel, and the predetermined fluid flow velocity is between approximately 10 and 100 centimeters per second.

5. A system as recited in claim 1 wherein the conduit of the chemostat and the conduit of the plug flow reactor each have a depth in a range between about 5 and 100 centimeters.

6. A system as recited in claim 1 wherein the residence time for the chemostat is 1-10 days and the residence time for the plug flow reactor is 1-4 days.

7. A system as recited in claim 1 wherein the algae growth removed from the plug flow reactor has an oil content of more than 60% of the dry weight of the algae growth.

8. A system as recited in claim 1 wherein the plug flow reactor receives effluence with algae growth from a plurality of chemostats.

9. A system as recited in claim 1 wherein a limited amount of a predetermined constituent in the modified nutrient mix triggers flocculation of the algae in the plug flow reactor.

10. A device for creating triglycerides in algae comprising:
    a first stage reactor for growing algae cells, said first stage reactor having an input port for receiving a medium with a nutrient mix for facilitating algae cell growth, an open raceway conduit with a paddlewheel means for continuously moving the medium and algae cells through the first stage reactor, and an output port for passing an effluence with algae cells from the first stage reactor;
    a second stage reactor for treating the algae cells, said second stage reactor having an input port for receiving the effluence with algae cells from the output port of the first stage reactor, and an open raceway conduit for continuously moving the effluence and algae cells downstream under the influence of gravity;
    a trigger means for activating triglyceride production in said algae cells in the conduit of the second stage reactor; and
    an algae separator for removing the algae cells from the conduit of the second stage reactor.

11. A device as recited in claim 10 wherein said first stage reactor is a continuously-stirred flow reactor, and wherein nutrients are selectively added to replenish the medium during cell growth.

12. A device as recited in claim 10 wherein said trigger means limits a supply of a nutrient to cause triglyceride production in the algae cells.

13. A device as recited in claim 12 wherein said nutrient is selected from a group consisting of nitrogen and phosphorous.

14. A device as recited in claim 10 wherein said trigger means is a first trigger means and further comprising a second trigger means for causing flocculation of the algae cells.

* * * * *